United States Patent [19]

Mizoue et al.

[11] Patent Number: 4,902,781
[45] Date of Patent: Feb. 20, 1990

[54] NOVEL TRIPETIDE DERIVATIVES

[75] Inventors: Kazutoshi Mizoue; Tadayasu Okazaki, both of Urawa; Kazunori Hanada; Sadafumi Omura, both of Ageo; Toshiro Amamoto, Omiya, all of Japan

[73] Assignee: Taisho Pharmaceutical Co., Ltd., Japan

[21] Appl. No.: 273,944

[22] Filed: Nov. 21, 1988

[30] Foreign Application Priority Data

Nov. 24, 1987 [JP] Japan .................................. 62-295579
Dec. 4, 1987 [JP] Japan .................................. 62-306934

[51] Int. Cl.$^4$ ................................................ C07K 5/08
[52] U.S. Cl. .................................................... 530/331
[58] Field of Search ........................................... 530/331

[56] References Cited

U.S. PATENT DOCUMENTS

| | | | |
|---|---|---|---|
| 4,428,875 | 1/1984 | Barbieri | 530/331 |
| 4,563,305 | 1/1986 | Ryan et al. | 530/331 |
| 4,582,639 | 4/1986 | Matson et al. | 530/331 |
| 4,672,106 | 6/1987 | Hamaoka et al. | 530/331 |

Primary Examiner—Lester L. Lee
Attorney, Agent, or Firm—Lorusso & Loud

[57] ABSTRACT

Tripeptide derivatives of the formula

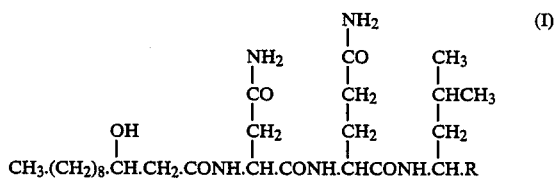

wherein R is a formyl group or a dimethoxymethyl group have antitumor and enzyme inhibition effects.

1 Claim, 6 Drawing Sheets

NOVEL TRIPETIDE DERIVATIVES

BACKGROUND OF THE INVENTION

1. Field of the Invention

The present invention relates to novel tripeptide derivatives and more particularly relates to novel tripeptide derivatives having antitumor effect and enzyme inhibition effect.

2. Prior Art

Peptides having antitumor effect are reported in Japanese Patent Kokai Nos. 120559/1982, 192349/1982, 8826/1984, 112953/1984 and the like, and bestatin is a commercially available as a peptide at present.

On the other hand, leupeptin and E-64 in U.S. Pat. No. 3,911,111 are known as peptides having inhibition effect on cathepsin B.

Since malignant tumors have indefinite variety in nature, there is a need for the development of novel antitumor agents.

It is known that cathepsin B is a proteolytic enzyme implicated in bone metabolic disorders, lysosomal disease, muscular dystrophy and metastasis of cancer. However, since most of the prior art inhibitors of cathepsin B have also inhibiting activity to other proteolytic enzymes, there is a need for the development of substances having specific inhibition of cathepsin B.

SUMMARY OF THE INVENTION

As a result of continuous research to obtain novel physiologically active substances from strains which are isolated from soil samples, the present inventors have found that the specific microorganism obtained by the present inventors produces substances having an inhibiting effect on the increase of cancer culture cells and a specific effect on cathepsin B.

An object of the present invention is to provide tripeptide derivatives of the formula

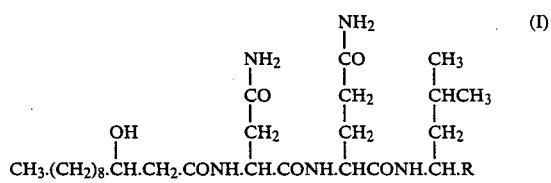

wherein R is a formyl group or a dimethoxymethyl group.

DETAILED DESCRIPTION OF THE INVENTION

Figure 1:
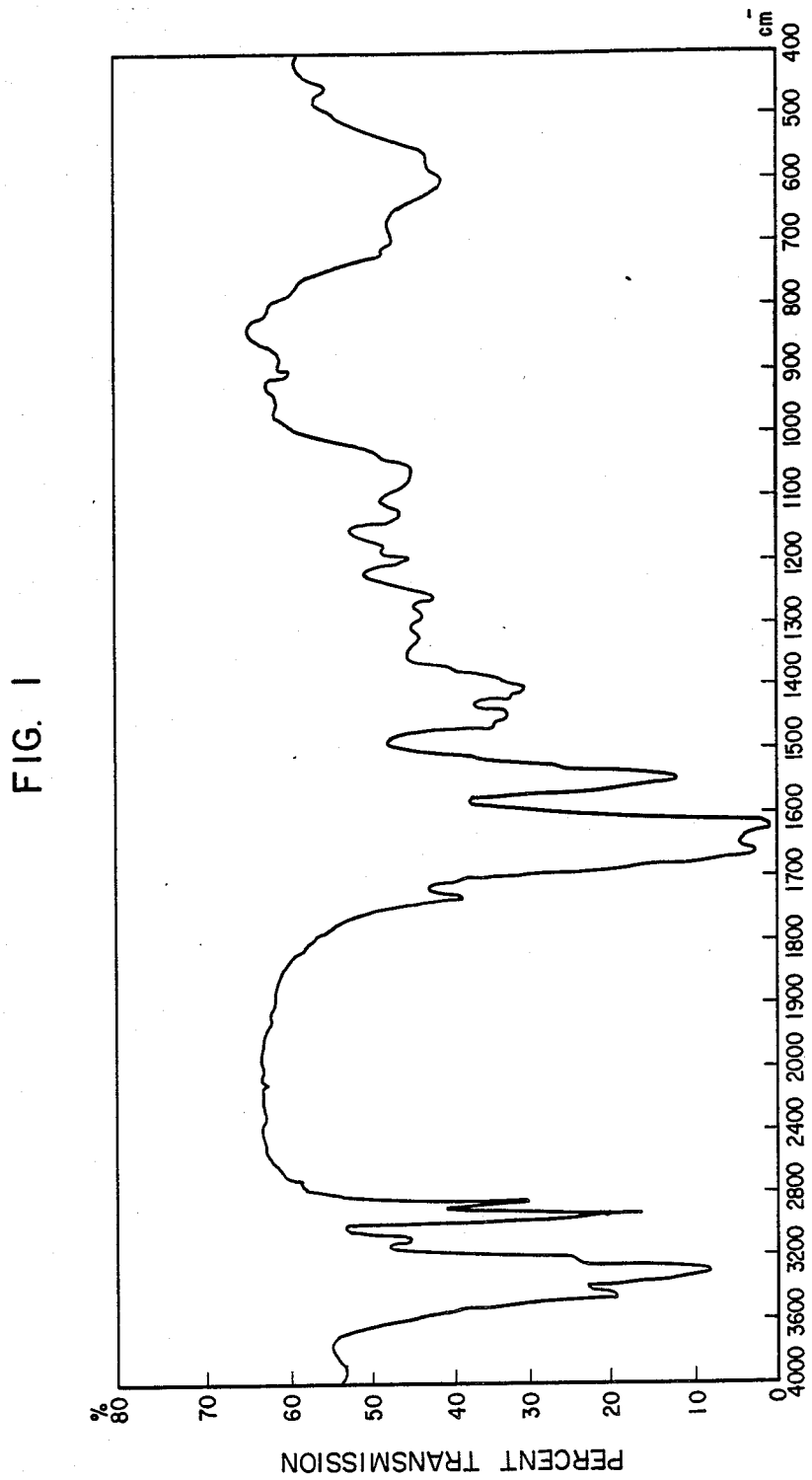
FIG. 1 shows the IR spectrum of 1656B measured in a KBr pellet.

The strain being capable of producing the compounds of the present invention (hereinafter the compound of Formula I wherein R is a formyl group is referred to as "1656B", and the compound of Formula I wherein R is a dimethoxymethyl group is referred as to "1656C") was newly isolated from a soil sample collected by the present inventors at Kamigyo-ku Kyoto city, Japan, and has been deposited with Fermentation Research Institute, the Agency of Industrial Science and Technology under the name of "Asperqillus species F1656" with deposition number "Ferm BP-1502".

The morphological properties of this strain are as follows:

(1) Morphology

This strain grows well on malt extract agar medium, potato-glucose agar medium and YpSs agar medium, and conidia also form well. At the stationary phase of the growth, the formation of ascocarp is observed on various media. Microscopic observation of colonies on potato-glucose agar medium is as follows: the hyphae are clear, septate and highly branched, the conidia stalks arise on the basal mycelium with branching, vary in size ranging $60-125\mu \times 9\mu \times 2.5\mu$ and have smooth walls. The vesicles are flask-shaped and vary from 9.5 to $15\mu$ in position of about ½ the way along the length of the vesicles. The basal phialides are $5-6\mu \times 2-3\mu$ in diameter, and apical phialides are $5-7 \ \mu \times 2-2.5\mu$ in diameter.

One phialo-type conidium adheres first at the apex of the phialide, and in the course of cultivation, becomes chained to form short cylindrical condial heads of $5-100\mu \times 30-40\mu$ in length. By electron microscopic observation, the conidia are spherical in shape, $3-3.5\mu$ in diameter, and from smooth to slightly rough in surface.

The ascogenesis is observed about 10 days after the cultivation. Dark reddish brown microfringed Hüll cells form in the center of the medium or in the peripheral surface. These fringes consist of hall cells each covering one to two or more of closed ascocarps. The Hüll cell is spherical in shape with thick wall, glass-like and $18-25\mu$ in diameter. The closed ascocarps are from spherical to subspherical in shape with thick wall, almost colorless on the first day but turn into reddish violet and then black by the passage of time, and $150-250\mu$ in diameter. The asci are from spherical to subspherical in shape, $8-12.5\mu$ in diameter, and have 8 ascospores which are lens-shaped, reddish violet in color, $4.0-8.0\mu$ in diameter, circularly peripheral and slightly recurved, and have regular pleats radiately. The lens is smooth surfaced.

(2) Properties on media

The cultivation was carried out on various media at 30° C. for 14 days, and the results of the macroscopic observation are shown in Table 1.

TABLE 1

| Medium | Growth of Medium | Color of Reverse Side of Colonies | Conidia Formation | Conidia Color | Soluble Pigment |
|---|---|---|---|---|---|
| Malt extract agar medium | good; 57 mm felt | pale brown | moderate | mustard | negative |
| Potato-glucose agar medium | good; 57 mm snowy crystallized | dark brown | good | pale green | negative |
| Czapek agar medium | moderate; 28 mm felt | creamy | moderate | ivory | pale purple |
| Sabouraud's agar medium | good; 60 mm vertically wrinkled velvety | brown | good | cork-colored | negative |
| Oatmeal agar medium | good; 50 mm annual ring-shaped | pale brown | good | dark green | pale purple |
| Synthetic mucor agar medium | moderate; 26 mm felt | pale brown | good | mustard | negative |
| $Y_pS_s$ agar medium | good; 45 mm felt | orange | good | dark green | negative |

Ascocarps are observed in all of the media at the stationary phase of the growth.

3. Physiological and Ecological Properties (1) Optimum growth

Optimum growth of this strain is at pH 4.9 to 9.3 at 27° to 37° C. on a YpSs medium.

(2) Growth range:

Growth range of this strain is at pH 3.8 to 9.8 at 15° to 40° C. on a YpSs medium.

(3) Distinction between aerobic or anaerobic: aerobic

It is apparent from the above-mentioned morphological and properties on the cultivation that this strain belongs to genus Aspergillus. These properties were compared with those of many strains reported by Shun-ichi Udagawa and Keisuke Tsubaki in "The Illustration of Fungi" (1978), and by Raper and Fennell in "The Genus Aspergillus" (1965). As a result of the above, this strain was found to have the most similar properties to those of *Asperqillus nidulans (Eidam) Wint.*

However, this strain is slightly different from *Asperqillus nidulans (Eidam) Wint* described in the literature in the shape of the conidial surface, and therefore, this strain was of undetermined species, and was named as Asperqillus sp. F-1656.

The new tripeptide derivatives, 1656B and 1656C can be prepared by following procedures similar to those used for producing common fermentation products.

Namely, the Asperqillus sp. F-1656 strain is cultivated in medium containing various nutrient substances under aerobic conditions.

A liquid medium is mainly used, the carbon sources used for the medium are glucose, molasses, starch and the like, and they are used alone or in admixture. The nitrogen sources used are polypeptone, soybean meal, yeast extract and the like, and they are used alone or in admixture. Furthermore, if necessary, organic substances or inorganic salts can be used in order to aid the growth of the strain and to promote the formation of novel tripeptide derivatives, 1656B and 1656C.

Adekanol, silicone and the like can be used as the defoaming agents.

Preferred cultivations are aerobic cultivations such as shake cultivation and aerobic stirring cultivation at pH 3-7 at 25°-37° C. for 2-5 days, preferably at pH 6-7, at 28°-30° C. for 3-4 days.

Isolation of the tripeptide derivatives of Formula I thus obtained in the fermentation broth can be carried out according to an ordinary method by which the fermentation products are collected. Namely, after completion of the cultivation, the fermentation broth is collected by centrifugation or filtration, and the resulting culture filtrate is absorbed on Dia-ion HP-20 (trade name, Mitsubishi Chemical Industries Co.) and the like and eluted with a lower alcohol. The eluted fractions of the tripeptide derivatives of Formula I are concentrated, dissolved in a water-insoluble solvent such as ethyl acetate, chloroform and the like, and the solution is concentrated to give a syrup. The syrup is further dissolved in an organic solvent such as ethyl acetate, chloroform and the like, and the solution is subjected, in turn, to column chromatography using silica gel, gel filtration using Sephadex LH-20 (trade name, Pharmacia Co.) and column chromatography using Chromatorex (trade name, Fuji—Davison Co.) to collect the active components, thereby isolating the tripeptide derivatives of Formula I in each pure forms.

A novel tripeptide derivative 1656B obtained by the purification described above has the following physiochemical properties and structure assumed.

(1) Appearance: white powder.

(2) Melting point: 185°–186° C.

(3) Quantity analysis value

Cation FABMS spectrum: m/z 556 (M+H)

Anion FABMS spectrum: m/z 554 (M−H).

(4) High resolution mass FABMS spectrum: m/z 556 (M+H) m/z Found 556.3654 for $C_{27}H_{50}N_5O_7$, Calcd. 556.3598.

(5) Molecular formula: $C_{27}H_{49}N_5O_7$.

(6) $[\alpha]_D^{26}$: −22.8 (c=0.1 methanol solution).

(7) UV absorption spectrum

When measured in an ethanol solution, an end absorption is indicated.

(8) IR absorption spectrum

A spectrum measured in a KBr tablet is shown in FIG. 1.

Figure 2:
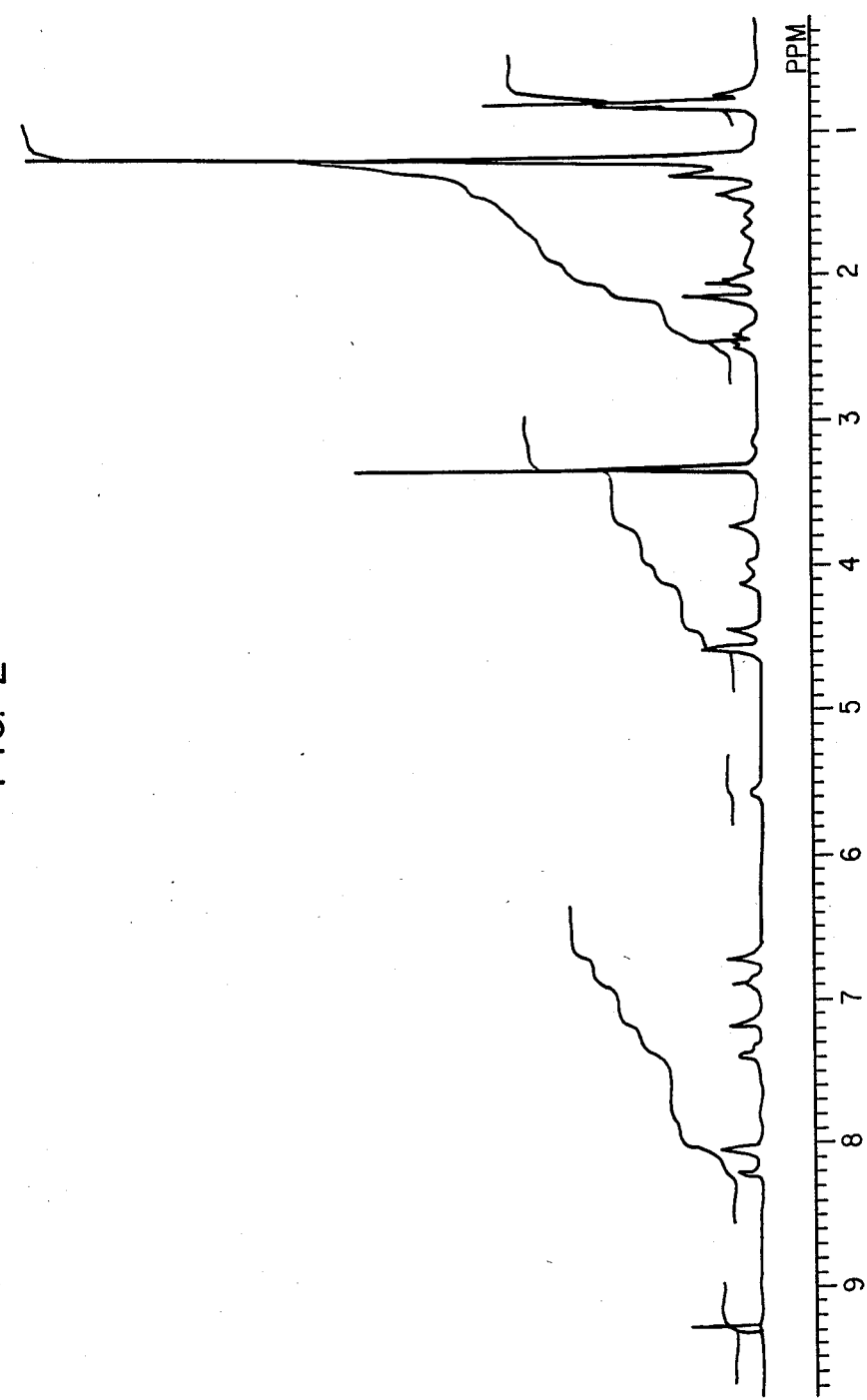
FIG. 2 shows the $^1$H—NMR spectrum of 1656B measured in $(CD_3)_2SO$ ($DMSO-d_6$) at 400 MHz.

(9) $^1$H NMR spectrum:

A spectrum measured in $d_6$—DMSO at 400 MHz is shown in FIG. 2.

Figure 3:
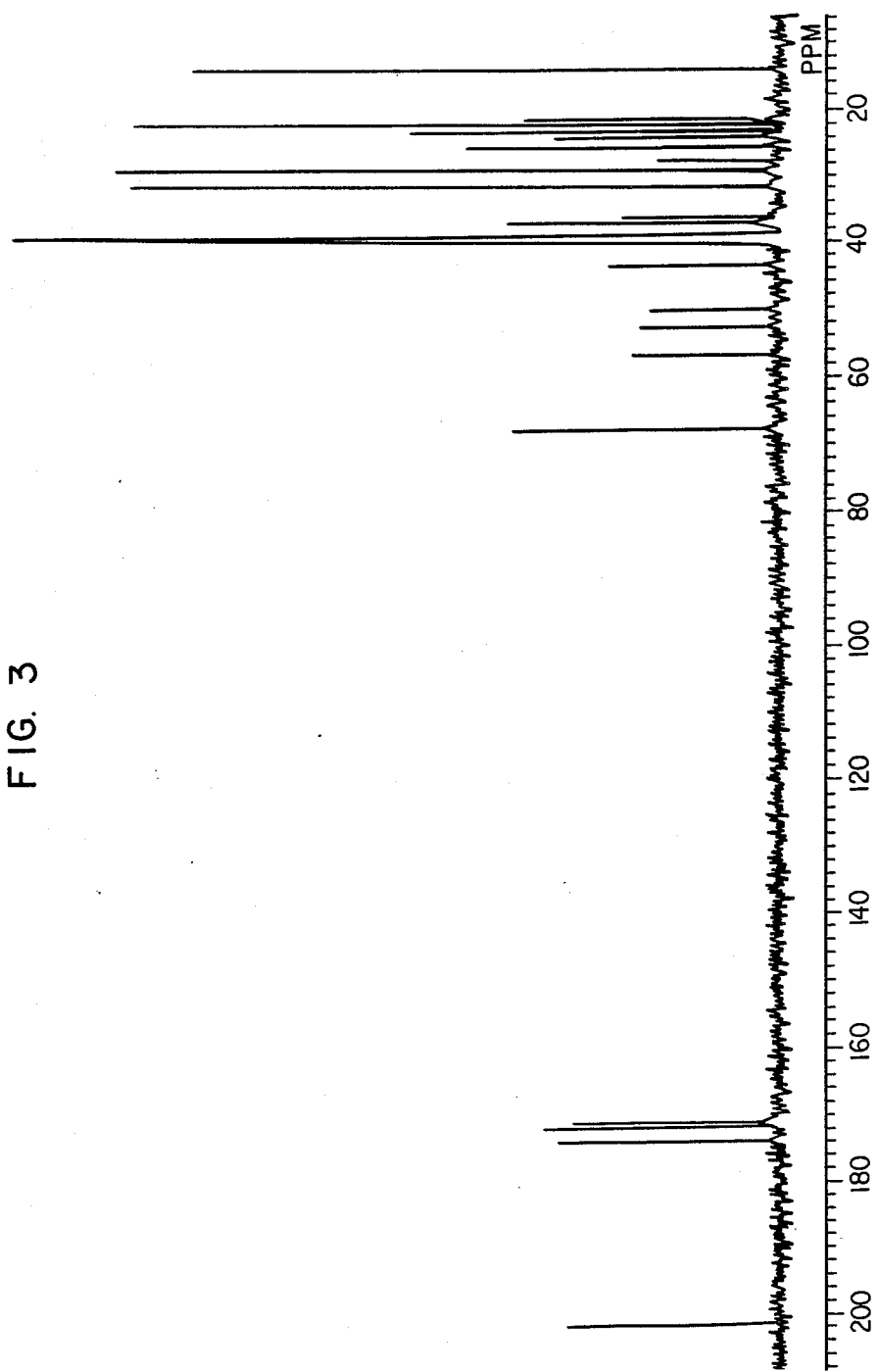
FIG. 3 shows the $^{13}$C—NMR spectrum of 1656B measured in $DMSO-d_6$ at 100 MHz.

(10) $^{13}$C NMR Spectrum:

A spectrum measured in $d_6$—DMSO at 100 MHz is shown in FIG. 3.

(11) Solubility:

Easily soluble in methanol, acetic acid and DMSO. Poorly soluble in ethyl acetate, chloroform and acetone. Insoluble in n-hexane, petrolium ether, ethyl ether and water.

(12) Color reaction

Positive with iodide, Rydon-Smith, 2,4-dinitrophenyl hydrazine (2,4-DNP), triphenyltetrazorium chloride (TTC). Negative with sulfuric acid, anisaldehyde-sulfuric acid, vanilin-sulfuric acid and ninhydrin.

(13) Distinction between basic, acidic and neutral: neutral.

(14) Structure

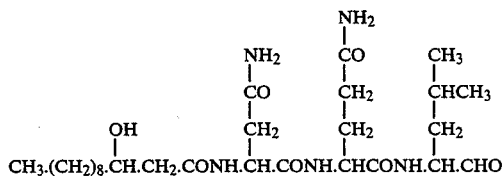

A novel tripeptide derivative 1656C has the following physiochemical properties.

(1) Appearance: white powder.
(2) Melting point: 220°–221° C.
(3) Quantity analysis value
Cation FABMS spectrum: m/z 602 (M+H)
Anion FABMS spectrum: m/z 600 (M−H).
(4) Elemental analysis: Found C: 57.90%, H: 9.15%, N: 11.64% for $C_{29}H_{55}N_5O_8$ Calcd. C: 56.73%, H: 9.12%, N: 11.26%.
(5) Molecular formula; $C_{29}H_{55}N_5O_8$.
(6) $[\alpha]_D^{26}$: −25.3 (c=0.1 methanol solution).
(7) UV absorption spectrum When measured in an ethanol solution, an end absorption is indicated.

(8) IR absorption spectrum

Figure 4:
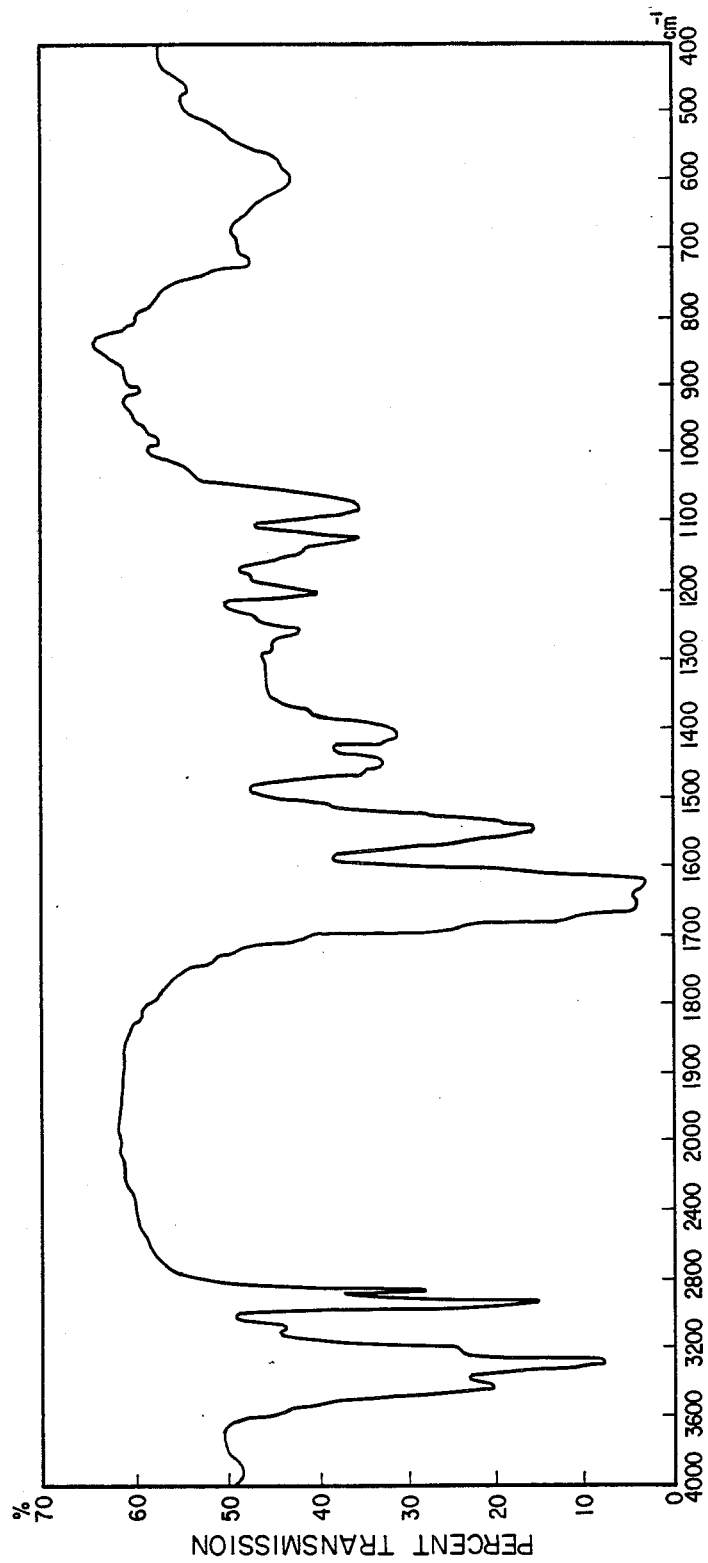
FIG. 4 shows the IR spectrum of 1656C measured in a KBr pellet.

A spectrum measured in a KBr tablet is shown in FIG. 4.

Figure 5:
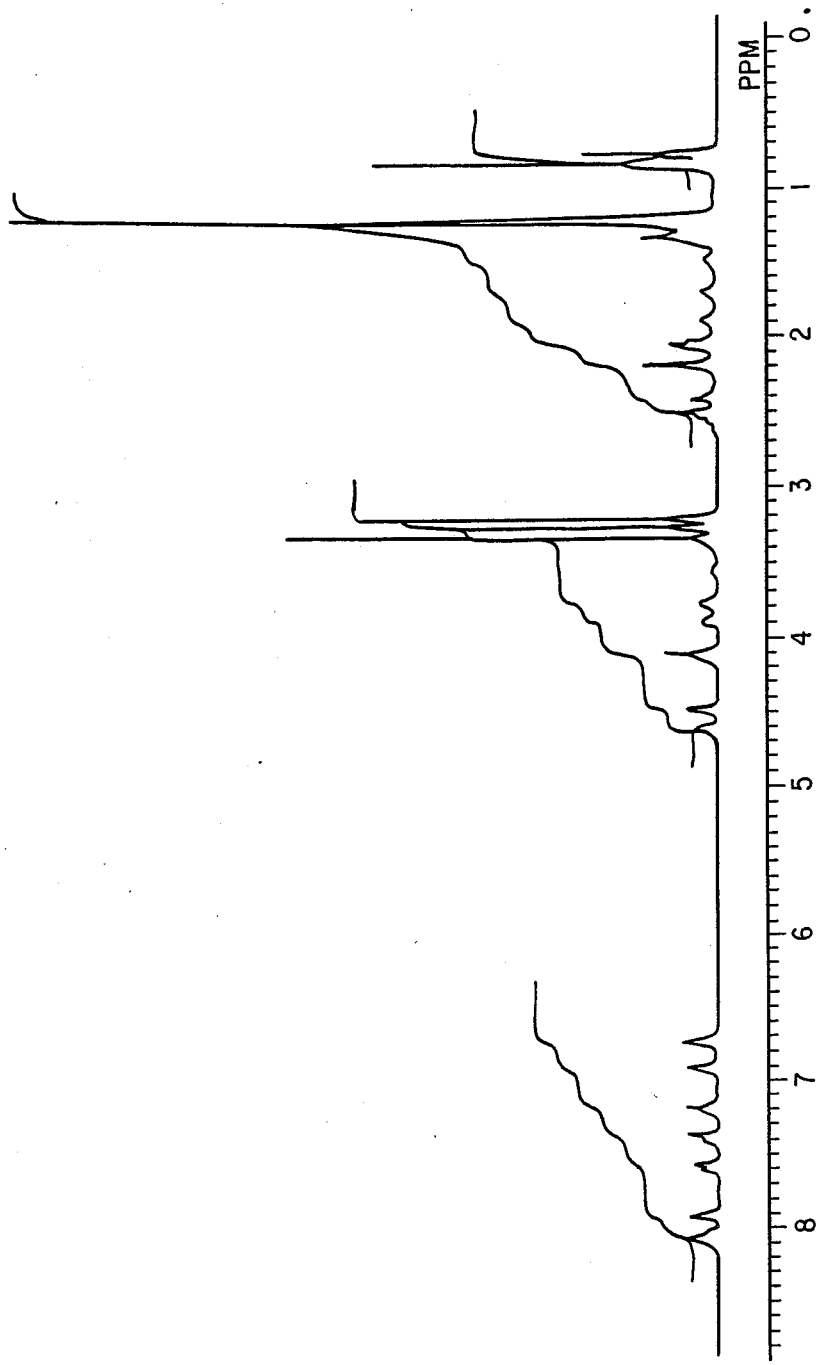
FIG. 5 shows the $^1$H—NMR spectrum of 1656C measured in $DMSO-d_6$ at 400 MHz.

(9) $^1H$ NMR spectrum:

A spectrum measured in $d_6$—DMSO at 400 MHz is shown in FIG. 5.

Figure 6:
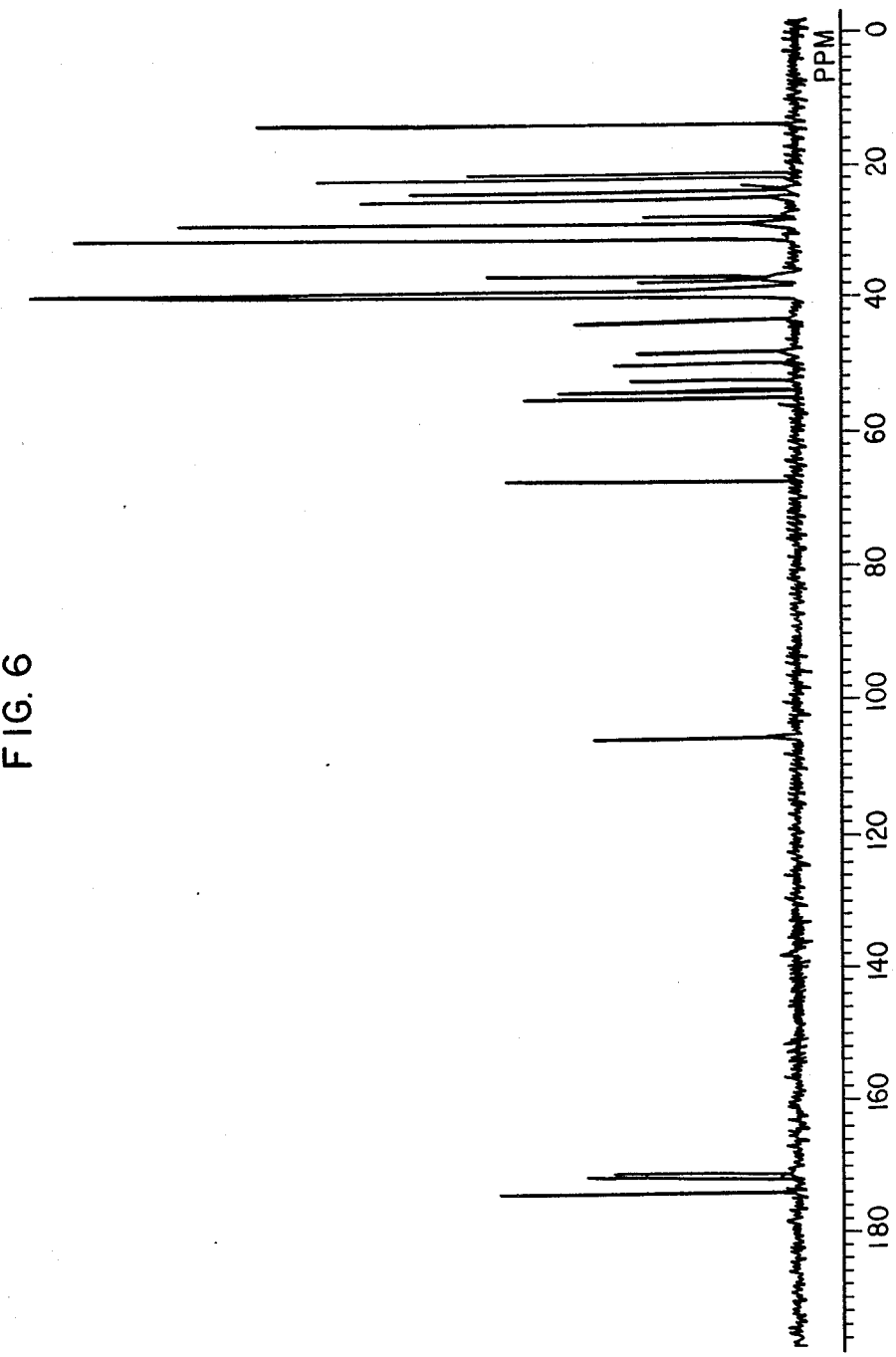
FIG. 6 shows the $^{13}$C—NMR spectrum of 1656C measured in $DMSO-d_6$ at 100 MHz.

(10) $^{13}C$ NMR spectrum:

A spectrum measured in $d_6$—DMSO at 100 MHz is shown in FIG. 6.

(11) Solubility:

Easily soluble in methanol, acetic acid and DMSO. Poorly soluble in ethyl acetate, chloroform and acetone. Insoluble in n-hexane, petroleum ether, ethyl ether and water.

(12) Color reaction

Positive with iodide, Rydon-Smith. Negative with sulfuric acid, anisaldehyde-sulfuric acid and ninhydrin.

(13) Distinction between basic, acidic and neutral: neutral

(14) Structure

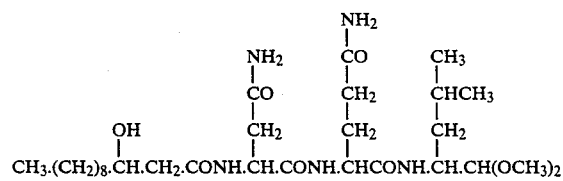

Novel tripeptide compounds of the present invention inhibit growth of cancer culture cells, and have specific inhibition effect on cathepsin B, therefore, they are useful as antitumor agents, and drugs for bone metabolic disorder, lysosomal disease, muscular dystrophy and metastasis of cancer. For these purposes, these compounds alone or in admixture with pharmaceutically acceptable carriers can be administered orally or parenterally. Examples of the pharmaceutically acceptable carrier for oral administration are sugars (e.g., milk sugar, mannitol and the like), starches, crystalline cellulose, potassium citrate, potassium phosphite, gelatin, dextrin, methylcellulose, sodium carboxymethylcellulose, hydroxypropylcellulose, polyvinylpyrrolidone, stearic acid, magnesium stearate, calcium stearate, talc and the like. Examples of the pharmaceutically acceptable carrier for parenteral administration are vegetable oils, ethanol, propylene grycol, polyethylene glycols, cacao oil, laurin fat, glycerol and the like.

Dosage forms may be solid forms such as tablets, powders and capsules, and liquid forms such as solutions and suspensions. When administered parenterally, injectional preparations, dropping injectional preparations and suppositories can be used.

Dosage amount of the compound of the present invention depends on the administration route, the kind and degree of diseases, and age, body weight and conditions of patient, but usually it is from 0.3–30 mg/kg, preferably 1–20 mg/kg for oral administration, 0.1–10 mg/kg, preferably 0.5–5 mg/kg for intravenous administration.

EXAMPLE 1

(Preparation of 1656B)

(1) Aspergillus species F1656 strain was inoculated into a sterilized liquid medium containing 4 g of glucose and 1 g of polypeptone per 100 ml and shake cultivation was carried out at 30° C. for 96 hours. Then, 0.6 l of the above fermentation broth was seeded into 30 l of a sterilized medium having the same components as those of seed cultivation using a 50 l jar fermentor, and fermentation was carried out under aerobic conditions at 30° C. for 72 hours.

(2) After completion of the fermentation, 85 l of the fermentation broth obtained using 3 jar fermentors was filtered out, and 80 l of the filtrate thus obtained was absorbed on 2.5 l of Dia-ion HP-20 (trade name, Mitsubishi Chemical Industries Co.) and eluted with 5 l of 75% methanol. The eluate was concentrated to a volume of 1 l, and the concentrate was extracted twice with an equal volume of ethyl acetate. The ethyl acetate layers obtained from the filtrate and the ethyl acetate layers obtained from the mycelium were combined, dried over anhydrous sodium sulfate, and concentrated to give 12 g of a brown syrup.

(3) Twelve ml of the syrup was dissolved in 50 ml of methanol and subjected to gel filtration by methanol using a 2 l column packed with Sephadex LH-20 (trade name, Pharmacia Co.) prepared with methanol. The active fractions were collected to give 8 g of a light brown syrup.

(4) The light brown syrup in the above item was dissolved in 100 ml of chloroform-methanol (85:15), absorbed on a column packed with 200 ml of silica gel (Kieselgel-60, trade name, Merck Co.) prepared with chloroform-methanol (85:15) and washed with 400 ml of a mixture of chloroform and methanol (85:15). The fractions eluted with 600 ml of a mixture of chloroform and methanol (75:25) were combined and concentrated to dryness to give 700 mg of a crude powder.

(5) Seven hundred mg of the crude powder obtained in the above item was dissolved in 10 ml of mixture of methanol-water-trifluoroacetic acid (80:20:0.1), and applied to Chromatorex (trade name, Fuji-Davison Chemical Co.) prepared with a solvent having the same components as described above, and eluted with a solvent having the same components as described above. The resulting active fractions were collected and neutralized with 1N sodium hydroxide and concentrated to dryness to give 300 mg of a white powder. In 6 ml of methanol was dissolved the powder, and the solution was subjected to gel filtration by methanol using a Sephadex LH-20 column (trade name, Pharmacia Co.). The resulting active fractions were collected and concentrated to dryness to give 120 mg of white powders. As a result of measurement, the melting point of this white powder was 185°–186° C.

EXAMPLE 2

(Preparation of 1656C)

In 10 ml of a mixture of methanol-water obtained by the procedures of Example 1 (1)–(4), the solution was applied to Chromatorex (trade name, Fuji-Davison Chemical Co.) prepared with a solvent having the same components as described above, and eluted with a solvent having the same components as described above. The resulting active fractions were collected and concentrated to dryness to give 80 mg of a white powder, which was then dissolved in 10 ml of a mixture of methanol-water (80:20). The solution was applied to a reverse phase high performance liquid chromatography (Develosil, 10 mm in diameter×25 cm long, Senshu Science Co.) at a column temperature of 40° C. and at a flow rate of 4 ml/minute, and eluted with 75% methanol. The elution was repeated, and the fractions having a retention time of about 14 minutes were collected and concentrated to dryness to give 35 mg of a white powder, which was then dissolved in 3 ml of methanol. The solution was subjected to gel filtration by methanol using Sephadex LH-20 (trade name, Pharmacia Co.). The resulting active fractions were collected and concentrated to dryness to give 30 mg of white powders. As a result of the measurement, the melting point of this powder was 220°–221° C.

EXAMPLE 3

A mixture of 6 g of 1656B, 90 g of milk sugar and 72.5 g of corn starch was granulated using 10 g of hydroxypropyl cellulose as a binding agent, 1.5 g of magnesium stearate was added, and then tablets each 8 mm in diameter and 180 mg in weight were prepared by means of a tablet machine.

EXAMPLE 4

Five g of 1656B and 95 g of corn starch were mixed well, and the mixture was sieved through a screen of 42 mesh to give powders.

EXAMPLE 5

To about 0.8 ml of injectional distilled water were added 5 g of 1656B and 40 g of D-sorbitol, and the mixture was stirred to give a solution, which was then added to distilled water to total volume of 1 l. The solution was filtered through a membrane filter of 0.22 μm in caliber, dispensed into 2 ml ampoules, sealed, sterilized by heating in a conventional manner to give an injectional preparation.

EXAMPLE 6

A mixture of 10 g of 1656C, 80 g of milk sugar and 73.5 g of corn starch was granulated using 5 g of hydroxypropyl cellulose as a binding agent, 1.5 g of magnesium stearate was added, and then tablets each 8 mm in diameter and 180 mg in weight were prepared by means of a tablet machine.

EXAMPLE 7

Ten g of 1656C and 90 g of corn starch were mixed well, and the mixture was sieved through a screen of 42 mesh to give powders.

EXPERIMENT 1

Multiplication inhibition effect of 1656B on various culture cells (Test drugs)

In methanol was dissolved 10 mg of the white powder obtained in Example 1, and the solution was diluted with sterilized physiological saline solution to desired concentrations.

(Test cells)

(1) P-388 leukemia in mouse
(2) L-1210 leukemia in mouse
(3) YAC-1 leukemia in mouse
(4) HL-60 leukemia in human
(5) K-562 leukemia in human
(6) KB mouth cancer in human
(7) KATO-III gastric cancer in human (Culture broth)

(1) RPMI-1640 medium
(2) Eagle MEM medium (Test procedure)

$2\times 10^4$–$1\times 10^5$/ml of the above cancer cells in the fermentation broth were dispensed in 2 ml into 6-pitted petridishes whose pits were 35 mm in diameter. Each 50 μl of the test drugs which were previously diluted to the desired concentration was added to the test cells (1), (2), (3), (4) and (5) at the same time as starting the cultivation at 37° C. in 5% oxygen culture vials, and to test cells (6) and (7) one day after the same cultivation.

The test cells (1), (2), (3), (4) and (5) were incubated for 3–4 days, and the test cells (6) and (7) were incubated for 7 days. The survival cells were counted, and the $IC_{50}$ values (concentration to require to 50% inhibitinn) were cultured from the concentration of the test solution and the inhibition rate.

(Results)

The results were shown in Table 2.

TABLE 2

| cell | $IC_{50}$ value (μg/ml) |
|---|---|
| P-388 | 0.44 |
| L-1210 | 0.80 |
| YAC-1 | 0.14 |
| HL-60 | 0.08 |
| K-562 | 0.14 |
| KB | 0.36 |
| KATO-III | 0.89 |

EXPERIMENT 2

(Antitumor effect of 1656B on P-388 leukemia in mouse)

(Test drug)

In 0.5% gum arabic/sterilized physiological saline was suspended 10 mg of the white powder obtained in Example 1 to desired concentration.

(Test animals)

Eight female $CDF_1$ mice, 6 weeks old, were used for each group. Twenty animals were used for control group.

(Test procedure)

Female $CDF_1$ mice were intraperitoneally transplanted with $1 \times 10^5$ cells of P-388 per mouse. From the day after transplantation, 0.2 ml of a suspension of the test drug adjusted to the desired concentration was administered intraperitoneally once a day, for 5 days. The effect of increasing lifespan was evaluated by calculated according to the criterion of the National Cancer Institute of the United States (NCI). The value of $T/C \times 100$ (%) was calculated from the median survival times for the treated animals (T) and the control animals (C).

(Results)

The results were shown in Table 3.

TABLE 3

| dose | T/C (%) |
|---|---|
| 50 | 33 |
| 12.5 | 144 |
| 3.13 | 121 |

EXPERIMENT 3

Multiplication inhibition effect of 1656C on various culture cells (Test drugs)

In methanol was dissolved 10 mg of the white powder obtained in Example 2, and the solution was diluted with sterilized physiological saline solution to desired concentrations.

(Test cells)

(1) HL-60 leukemia in mouse
(2) K-562 leukemia in human
(3) KB mouth cancer in human (Culture broth)

(1) RPMI-1640 medium
(2) Eagle MEM medium (Test procedure)

$2 \times 10^4 - 1 \times 10^5$/ml of the above cancer cells in RPMI-1640 medium were dispensed in 2 ml into 6-pitted petridishes whose pits were 35 mm in diameter. Each 50 μl of the test drugs which were previously diluted to the desired concentration was added to the test cells (1) and (2) at the same time as starting the cultivation at 37° C. in 5% oxygen culture vials, and to test cells (3) one day after the same cultivation. The test cells (1) and (2) were incubated at 37° C. in 5% oxygen culture vials for 3-4 days, and the test cells (3) were similarly incubated for 7 days. The survival cells were counted and the $IC_{50}$ values (concentration to require to 50% inhibition) were calculated from the concentration of the test solution and the inhibition rate.

(Results)

The results were shown in Table 4.

TABLE 4

| cell | $IC_{50}$ value (μg/ml) |
|---|---|
| HL-60 | 0.16 |
| K-562 | 2.06 |
| KB | 0.12 |

EXPERIMENT 4

(Inhibition activity against cathepsin B)

The test was carried out according to the method of A. J. Barrett and H. Kireschke described in "Methods in Enzymology", vol. 80, pages 535-561 (1981), Academic Press (New York).

To 0.25 ml of 0.4M—phosphoric acid buffer (pH=6.0) containing 8 mM—dithiothreitol and 4 mM—EDTA was added 0.5 ml of a solution of 10–100 ng of cathepsin B in 0.1% Briji 35, and then 10 mg/ml of dimethylsulfoxide solution of 1656B or 1656C was added to the desired concentration and incubated at 37° C. for 5 minutes.

Subsequently, Z-Phe-Arg-NMec was added and the mixture was allowed to react for 10 minutes, after which 0.1 M—acetic acid buffer (pH=4.3) containing 1 ml of 100 mM—sodium monochloroacetate was added to stop the reaction.

The inhibition concentration was determined by measurement of the free aminomethylcoumarin using a fluorescent photometer.

(Result)

The results are shown in Table 5.

TABLE 5

| Compound | 1656B | 1656C |
|---|---|---|
| $ID_{50}$ | 0.5 | 0.8 |

EXPERIMENT 5 (Acute toxicity test)

Ten male ICR strain mice, 5 weeks old, weighing about 20 g, were used for each group. Ten animals were also used for a control group. 1656B and 1656C were each dissolved or suspended in physiological saline to prepare the desired concentrations (1, 3, 9 and 27 mg/kg) of the test drugs. Physiological saline was only used for control. Each concentration of the test drug was administered peritoneally to mice once, and observation was continued for 7 days to determine 50% lethal dose ($LD_{50}$ value) according to the method of Litchfield-Wilcoxon. As the results, $LD_{50}$ values of 1656B and 1656C were each 30 mg/kg or more.

What is claimed is:

1. A tripeptide derivative of the formula

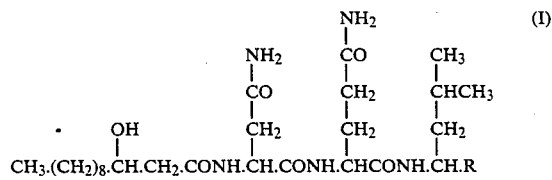

wherein R is a formyl group or a dimethoxymethyl group.

* * * * *

UNITED STATES PATENT AND TRADEMARK OFFICE
CERTIFICATE OF CORRECTION

PATENT NO. : 4,902,781

DATED : February 20, 1990

INVENTOR(S) : MIZOUE et al

It is certified that error appears in the above-identified patent and that said Letters Patent is hereby corrected as shown below:

Col. 2, line 34, after "in" insert --diameter, and parallel phialides form radiately at the--.

Signed and Sealed this

Twenty-fifth Day of June, 1991

Attest:

HARRY F. MANBECK, JR.

Attesting Officer

Commissioner of Patents and Trademarks